United States Patent [19]
Tockman et al.

[11] Patent Number: 5,540,727
[45] Date of Patent: Jul. 30, 1996

[54] METHOD AND APPARATUS TO AUTOMATICALLY OPTIMIZE THE PACING MODE AND PACING CYCLE PARAMETERS OF A DUAL CHAMBER PACEMAKER

[75] Inventors: Bruce A. Tockman, Minneapolis; Julio C. Spinelli, Shoreview; Rodney W. Salo, Fridley, all of Minn.

[73] Assignee: Cardiac Pacemakers, Inc., St. Paul, Minn.

[21] Appl. No.: 339,813

[22] Filed: Nov. 15, 1994

[51] Int. Cl.$^6$ .................................................. A61N 1/365
[52] U.S. Cl. ................................................ 607/18; 607/17
[58] Field of Search ................................. 607/18, 19, 20, 607/17, 32

[56] References Cited

U.S. PATENT DOCUMENTS

| | | | |
|---|---|---|---|
| 4,303,075 | 12/1981 | Heilman et al. | 607/14 |
| 4,553,547 | 11/1985 | Keimel | 607/17 |
| 4,674,518 | 6/1987 | Salo | 128/695 |
| 4,686,987 | 8/1987 | Salo et al. | 607/24 |
| 4,928,690 | 5/1990 | Heilman et al. | 607/4 |
| 5,054,485 | 10/1991 | Cohen | 607/4 |
| 5,170,794 | 12/1992 | Reiche | 128/723 |
| 5,334,222 | 8/1994 | Salo et al. | 607/23 |
| 5,350,409 | 9/1994 | Stoop et al. | 607/17 |
| 5,404,877 | 4/1995 | Nolan et al. | 607/20 |
| 5,423,867 | 6/1995 | Poore et al. | 607/17 |
| 5,423,869 | 6/1995 | Poore et al. | 607/18 |

OTHER PUBLICATIONS

Perry, J.G., Nanda N.C., "Evaluation of Pacemaker Dynamics by Doppler Echocardiography" Journal of Electrophysiology, 1(2):173–188, 1987.

Wish M., Fletcher, R.D., "Optimal Left Atrioventricular Sequence In Dual Chamber Pacing–Limitations of Programmed AV Larteral" Journal American College of Cardiology, 3:507A, 1984.

Julio C. Spinelli, Max E. Valentinuzzi, "Stroke Volume In the Dog: Measurements by the Impedance Technique and Thermodilution" Medical Progress Through Technology 10:45–53, 1983.

Julio C. Spinelli, Max E. Valentinuzzi, "High–sensitivity, high–linearity, low–leak, self–balanced cardiograph", Medical Progress through Technology, 9:239–245, 1983.

"Effective Breathing Pattern on Blood Pressure and Heart Rate Oscillations in Humans" by Laude, et al. Clinical & Experimental Pharmacology and Physiology (1993) 20, 619–626.

Margarete Hochleitener, et al., "Usefulness of Physiologic Dual–Chamber Pacing in Drug–Resistant Idiopathic Dilated Cardio–myopathy Am J. Cardiol" 1990; 66: 198–202.

*Primary Examiner*—William E. Kamm
*Assistant Examiner*—Carl H. Layno
*Attorney, Agent, or Firm*—Haugen and Nikolai, P.A.

[57] ABSTRACT

A cardiac stimulating system incorporating a microprocessor-based controller is designed to automatically optimize both the pacing mode and one or more pacing cycle parameters in a way that results in optimization of a cardiac performance parameter, such as cardiac output. For each of a plurality of modes in which a DDD cardiac pacer can operate, a pacing parameter such as the AV interval of the pacer is incrementally adjusted and following that, an observation is made as to the effect of the adjustment on cardiac output. After the process has been repeated for all possible pacing modes, a determination is made to find the pacing mode and the AV interval or other pacing parameter that results in the maximum cardiac output or other optimal cardiac performance parameter. It is these pacing parameters that are then programmed into the microcontroller for causing the pacemaker to function in the desired mode and at the desired parameter values.

9 Claims, 2 Drawing Sheets

METHOD AND APPARATUS TO AUTOMATICALLY OPTIMIZE THE PACING MODE AND PACING CYCLE PARAMETERS OF A DUAL CHAMBER PACEMAKER

BACKGROUND OF THE INVENTION

I. Field of the Invention

This invention relates generally to implantable, programmable, cardiac stimulating apparatus, and more particularly to a method for determining and manually or automatically programming the device so that it operates in a stimulating mode and with stimulating cycle parameters that optimize one or more cardiac performance parameters of the patient, such as, cardiac output, mean arterial pressure, $pO_2$ or $pCO_2$, etc.

II. Discussion of the Prior Art

A paper entitled "Usefulness of Physiologic Dual-Chamber Pacing in Drug-Resistant Idiopathic Dilated Cardiomyopathy" by Margarete Hochleitner, et al. (*Am J Cardiol* 1990; 66:198–202), describes the beneficial effects of dual-chamber (DDD) pacing on critically ill patients suffering from chronic heart failure. The patients involved in the underlying study were treated by implanting a DDD cardiac pacemaker whose atrial electrode was positioned near the right auricle and the ventricular electrode was positioned in the apical region of the right ventricle. The implanted pacemaker was programmed to have an atrioventricular (AV) interval of 100 ms when pacing in the DDD mode. The 100 ms AV interval was chosen as that offering the shortest possible delay that did not significantly impair cardiac function. The cardiac function was evaluated through echocardiographic studies and then the pacemaker was manually programmed to function with an AV delay of 100 ms as a compromise between a shorter value that resulted in poor right ventricular compliance and a larger value that failed to show any significant improvement in cardiac function. The Hochleitner paper describes in detail the marked improvement in cardiac performance of the CHF patients due to the DDD pacing at the 100 ms AV delay interval.

As is explained in a copending application of Julio C. Spinelli et al. Serial No. 07/339,815, filed Nov. 14, 1994, and entitled "Method and Apparatus to Continuously Optimize AV Delay in a Dual Chamber Pacemaker", patients exhibiting CHF typically have a very narrow range for the optimum AV delay, meaning that small deviations, e.g., only 10 ms, from the optimum can diminish the clinical benefit obtained using DDD pacing. Thus, arbitrarily setting the AV delay at a fixed programmed value, based upon echocardiographic data as set out in the Hochleitner paper, may not guarantee the optimum benefit obtainable to CHF patients using DDD pacing. It would, therefore, be advantageous to have a system that would automatically and periodically determine whether both the pacing mode and a controlled pacing cycle parameter are optimal for a given patient and, if not, they automatically, or with cardiologist intervention, effect a reprogramming of an implanted DDD pacemaker so that it is made to operate in a pacing mode and with a cardiac cycle parameter that results in an optimum benefit to the patient in terms of a measured cardiac performance parameter. Thus, for example, if the cardiac performance parameter of interest is cardiac output, it would be advantageous to have a programmable implantable DDD pacemaker whose AV delay and whose pacing mode results in a maximum cardiac output.

Accordingly, it is a principal object of the present invention to provide a cardiac stimulation device capable of dual chamber pacing and capable of operating in any one of a plurality of modes with the necessary implantable or external sensing/monitoring structure for iteratively altering a cardiac cycle pacing parameter, such as AV interval, between an initial value and a predetermined maximum value and for determining for each successive iterative change the associated value of the cardiac performance parameter being measured so that when all possible pacing modes and pacing cycle parameters have been utilized, a determination can be made as to which pacing mode and which cardiac cycle parameter achieved the optimum cardiac performance. Once that pacing mode and pacing cycle parameter is determined, the implanted cardiac stimulation device can be programmed to function in that mode and with that cycle pacing parameter.

SUMMARY OF THE INVENTION

The present invention provides an apparatus and method for establishing an optimum pacing parameter and pacing mode for an implantable programmable cardiac stimulating device. It comprises a physiologic parameter measuring means for evaluating at least one of a plurality of physiologic parameters including, for example, cardiac output, heart accelerations, mean arterial pressure, pulse pressure and partial pressure of respiratory gases in the patient's blood and producing signals proportional to average values thereof over a predetermined time interval that preferably includes an integral number of complete respiratory cycles. Control means are provided for periodically departing from a reference mode by incrementally changing a pacing parameter of the cardiac stimulating device by a predetermined value in a series of steps and storing the signals measured by the physiologic parameter measuring means in association with the particular value of the pacing parameter that produced the measured value. The algorithm employed also permits the control means to revert back to the reference mode to compensate for normal physiologic changes of the variables used for optimization. This obviates the need to pace the atrium to guarantee a steady state. Once the successive iterative incremental changes to the pacing parameter causes it to reach a predetermined limit, means are provided for comparing the signals stored during each iterative cycle to determine a maximum or minimum value thereof, depending upon the particular physiologic parameter involved. The implantable, programmable cardiac stimulating device is then programmed to operate with the pacing parameter value associated with the determined maximum or minimum value for the measured physiologic parameter.

In addition, the system of the present invention also provides a means for sequentially selecting one of a plurality of pacing modes for the implantable cardiac stimulating device. The physiologic parameter measuring device and the control means and comparing means mentioned above are operative to determine a maximum or minimum value of the stored signals for each of a plurality of pacing modes. Further means are then provided for setting the pacing mode of the cardiac stimulator to the particular mode that is associated with the maximum or minimum value of the stored signals, considering all of the plurality of pacing modes available.

DESCRIPTION OF THE DRAWINGS

The foregoing features, objects and advantages to the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
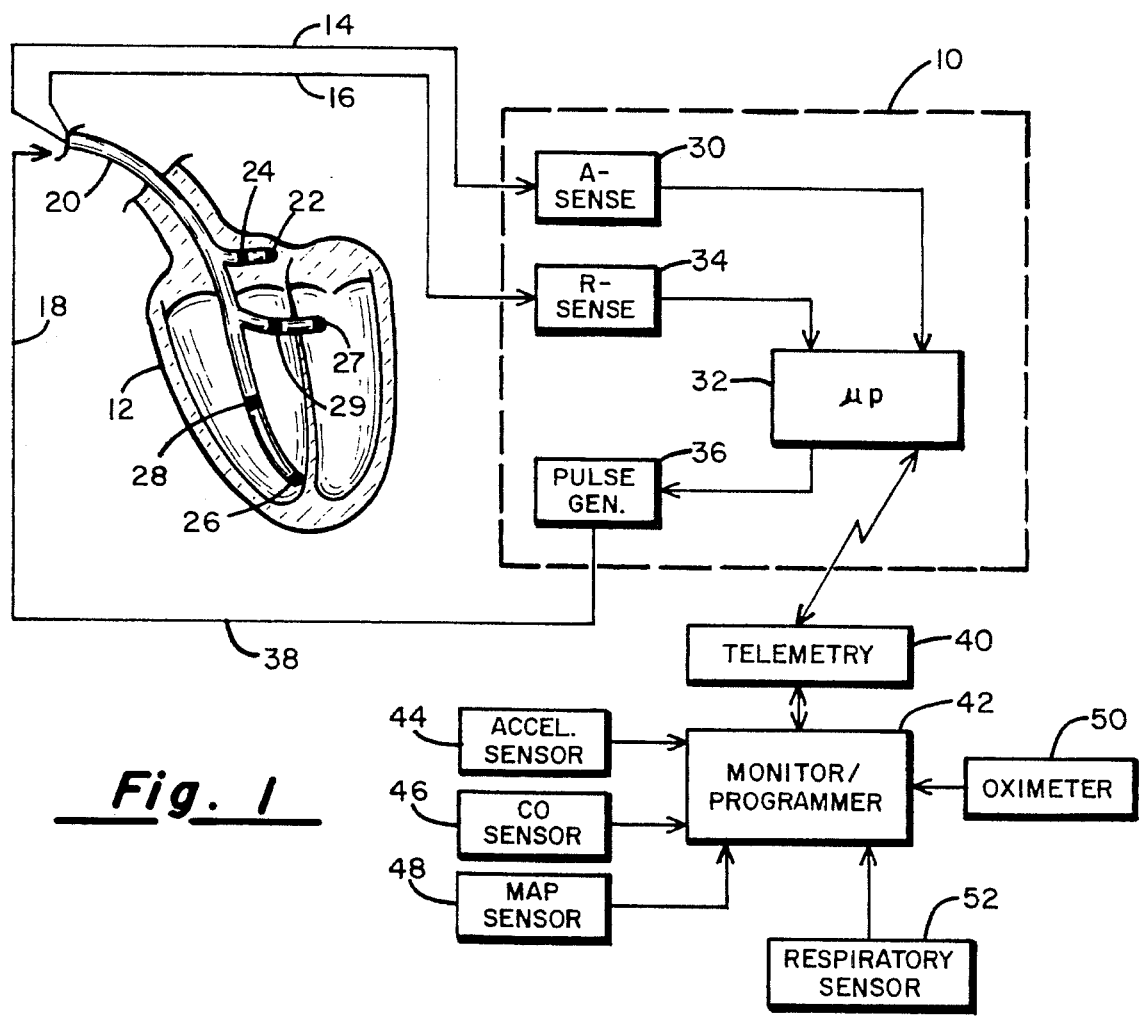
FIG. 1 is a block diagram of a DDD pacemaker and the associated external monitoring and programming devices comprising one embodiment of the invention.

Referring first to FIG. 1, there is illustrated by means of a schematic block diagram the components of the system comprising the present invention. It is seen to include an implantable, programmable DDD cardiac stimulating device or pacemaker 10 enclosed by dashed line box and which is operatively connected to a heart 12 by means of conductors 14, 16 and 18 embodied in a pacing lead 20. The pacing lead 20 includes an atrial branch having a first stimulating electrode 22 and a first sensing electrode 24 adapted to be disposed in the right atrium of the heart, a right ventricular branch having a second stimulating electrode 26 and a sensing electrode 28 and a coronary sinus branch with electrodes 27 and 29 for sensing and stimulating the left ventricle. The sensing electrode 24 is connected by the conductor 14 to an atrial sense amplifier 30 which is arranged to sense the occurrence of P-wave activity relating to atrial events. The resulting atrial event signal is then fed to an input of a microcontroller 32. In a similar fashion, the ventricular sense amplifier 34 is operatively coupled to electrodes 27 and 28 and functions to detect R-wave activity relating to right and left ventricular depolarization. The sense amplifier 34 also provides its output to the microcontroller 32.

The microprocessor 32 is programmed to operate in any one of a plurality of modes. For example, it can pace the atrium and pace either the right ventricle, the left ventricle or both the right and left ventricles when operating in a biventricular mode. It may also sense atrial activity and then pace the right, left or both of the ventricles. While FIG. 1 depicts a pacing/sensing lead in the right atrium and right ventricle, those skilled in cardiac rhythm management systems can configure leads for left ventricular and bi-ventricular pacing. In this regard, reference is made to the Mower U.S. Pat. No. 4,928,688, the teachings of which are incorporated by reference. The microprocessor 32 then controls the pulse generator 36 to deliver cardiac stimulating pulses to one or both of the stimulating electrodes 22 and 26 (depending upon the pacing mode selected) and establishes the relative timing for each, including the A-A interval, the V-V interval and the A-V interval.

The microprocessor 32 can also be programmed to establish the amplitude for the stimulating pulses delivered by the pulse generator over the lines 38 leading to the stimulating electrodes 22 and 26. Cardiac stimulating devices capable of telemetering various status information, via a telemetry link 40, to an external monitor/programmer 42 which also typically incorporates a microprocessor and associated memory are commercially available. Using the programmer 42 and the telemetry link 40, operating parameters for the DDD pacemaker 10 can be delivered to it by a cardiologist for setting the cardiac cycle pacing parameters to be utilized.

Also providing inputs to the monitor/programmer 42 are a plurality of cardiac performance monitoring devices including an acceleration sensor 44 capable of "listening" to cardiac heart sounds and providing signal characteristics of features of the mechanical movements of the heart muscle, its valves and the blood being pumped by it. Another cardiac performance parameter to be sensed is cardiac output, which may be derived from a cardiac output sensor 46. That sensor may typically comprise a Doppler flow sensor where the device is intended to be noninvasive.

Another indicator of cardiac performance is mean arterial pressure, and a pressure cuff or similar type sensor 48 may be used to provide a signal proportional to mean arterial pressure to the monitor/programmer 42. Similarly, a pulse oximeter 50 can be used to provide signals corresponding to the percentage concentration of oxygen and carbon dioxide in the patient's blood. A respiration sensor 52 capable of analyzing respiratory gases may be used to determine the partial pressure of oxygen and carbon dioxide, $pO_2$ and $pCO_2$ and deliver signals proportional thereto to the monitor/programmer 42.

Instead of using external equipment to sense various cardiac performance parameters, it is also contemplated that one or more sensors may be implanted within the body to directly provide inputs to the microprocessor 32 of the implanted DDD cardiac stimulator. In this regard, the electrodes 26 and 28 may be driven by a high frequency sine wave and then an impedance sensor may be used to derive an impedance signal due to the inflow and outflow of blood from the right ventricle in accordance with the teachings of the Salo U.S. Pat. No. 4,686,987. That patent teaches how cardiac output may be derived from the impedance signal. Furthermore, in that the impedance signal also carries a component related to respiratory activity, through appropriate signal processing, a signal can be derived from the impedance waveform proportional to inspiratory and expiratory activity of the patient.

A pressure sensor can also be implanted in the body where it would measure an appropriate pressure parameter such as right ventricular end-diastolic or end-systolic pressure. Such an implanted blood pressure sensor may also be used to derive respiratory information in that fluxuations in R-R interval and the systolic and diastolic pressures are known to comprise a respiratory component. For further information regarding the relationship between respiratory activity and blood pressure, reference is made to a paper entitled "Effective Breathing Pattern on Blood Pressure and Heart Rate Oscillations in Humans" by Laude, et al., *Clinical & Experimental Pharmacology and Physiology* (1993) 20, 619–626.

Figure 2:
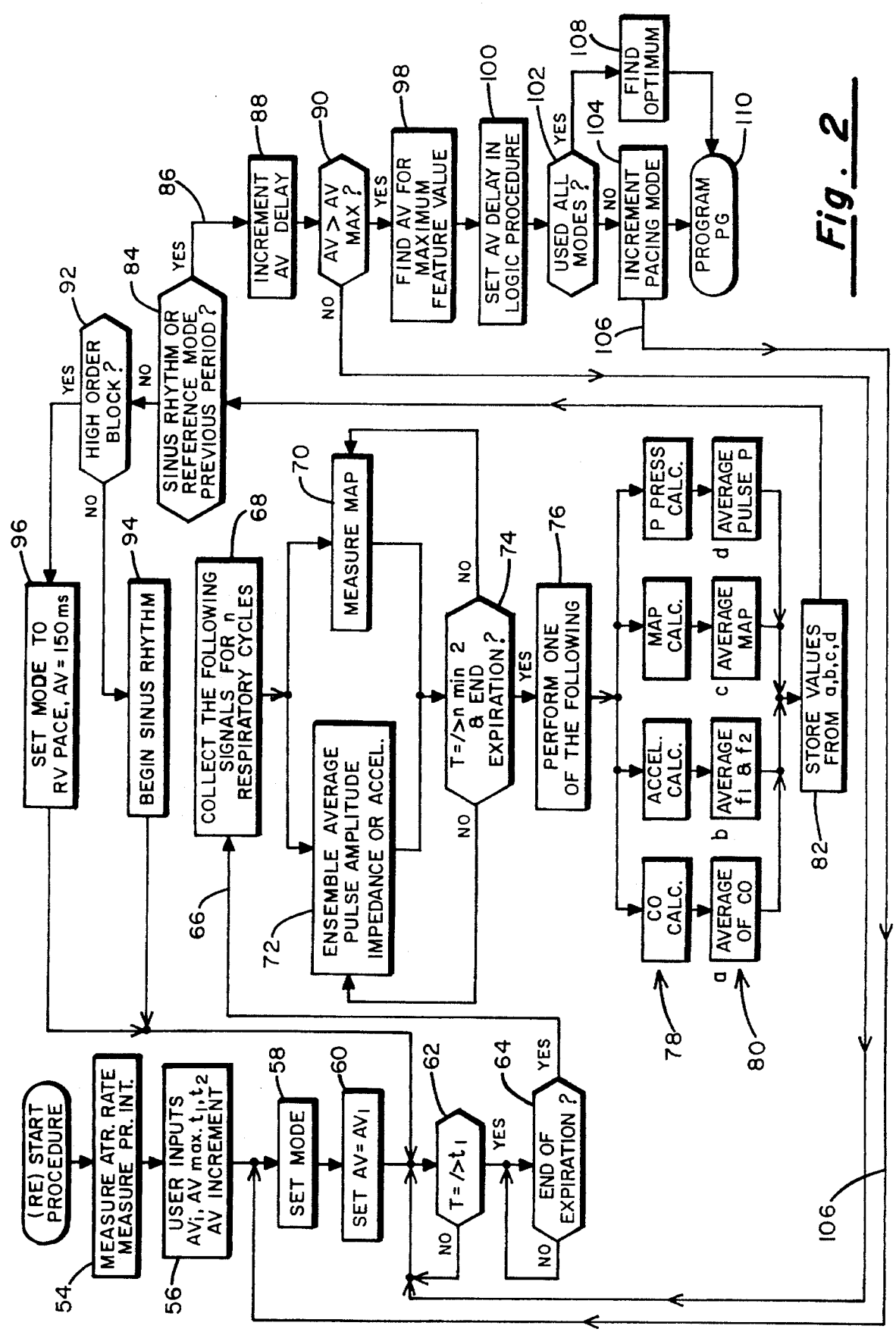
FIG. 2 is a software flow diagram illustrating the algorithm implemented either in the implantable portion of the system of FIG. 1 or embodied in the external equipment used therewith.

While the sensor components and devices described above are, for the most part, conventional, the manner in which they are used in combination with the DDD pacemaker is believed to be novel. Novelty also resides in the software implemented either in the microprocessor 32 of the implantable DDD pacemaker 10 or in the external monitor/programmer module 42. A flow chart of this software is depicted in FIG. 2. Persons having ordinary skill in the art having this flow chart and knowledge of the system configuration of FIG. 1 are in a position to write computer code for allowing the microprocessor to execute the algorithm represented by FIG. 2.

In explaining the invention, and especially the flow chart of FIG. 2, it is assumed that the pacing parameter of the cardiac stimulation device that is incrementally and periodically changed is the atrial-ventricular (A-V) delay interval. It should be emphasized that the invention is not to be limited to use in a system where only the A-V delay pacing parameter is modified and the results of the modification on physiologic parameters noted. For example, pacing parameters, such as pacing pulse width, the lower rate limit, the delay between right and left atrial stimulations ($A_R$- $A_L$ delay), the delay between right and left ventricular stimulations ($V_R$- $V_L$ delay), etc. may be subjected to incremental periodic changes with the effects on the body of such changes being noted and stored.

With the above understanding in mind and with reference then to FIG. 2, upon start-up of the optimization sequence, the microprocessor 32 first computes from signals from the sensor 30 the heart's atrial rate and from both sensors 30 and 34 its PR interval (see block 54). The external monitor/ programmer 42 and the telemetry link 40 may then be used to introduce user inputs, including an initial AV interval ($AV_i$), a maximum AV value ($AV_{max}$), the size of an AV increment ($\Delta AV$), measured in milliseconds, to be used and time values $T_1$ and $T_2$ measured in minutes. The entry of these user inputs is indicated by block 56 in FIG. 2.

At block 58 the DDD pacemaker's mode is set to one of the six possible modes. The a1 mode involves pacing the atrium and pacing the right ventricle. The a2 mode involves pacing the atrium and pacing the left ventricle. Mode a3 involves pacing the atrium and pacing both the left and right ventricles. In a similar fashion, the mode referred to b1 involves sensing atrial activity and pacing in the right ventricle. Modes b2 and b3 are likewise defined.

Let it be assumed that the pacing mode is randomly set to the a1 mode. Following that, the operation indicated by block 60 is carried out where the AV interval of the pacemaker 10 is set to the initial value $AV_i$ selected at block 56. Once that parameter has been set, the first time period, $t_1$, must expire during which time the patient's heart beat is allowed to stabilize. When the time, $t_1$, is reached, a test is made at block 64 to determine whether an expiratory phase of respiration has been completed. If not, the algorithm waits until it is. This insures that all subsequent measurements will be initiated with reference to the same point in a respiratory cycle, e.g., the end of expiration and the start of inspiration. Thus, variations in measurements occasioned by changes induced due to respiration will tend to be eliminated because the measurements always begin at the same point in the respiratory cycle.

Control then follows path 66 to the input of block 68. This block indicates that measurements are taken by the various cardiac performance parameter sensors 44–52 for an integral number of respiratory cycles taking place within the second time interval, $t_2$, that had been entered into the microprocessor at block 56. That is to say, the pressure sensor 48 measures mean arterial pressure at block 70 while the acceleration sensor 44 and the cardiac output sensor 46 provide inputs to the system as indicated at block 72. To eliminate transient, non-periodic noise, an ensemble averaging technique is preferably applied to the impedance and/or acceleration measurements. When the time interval, $t_2$, expires and a determination is made at decision block 74 that an end of the expiration phase of the respiratory cycle then in progress has been reached, the data gathered by the sensors are used to compute one of a plurality of possible cardiac performance parameters, including cardiac output, mean arterial pressure, pulse pressure, and these values are averaged over the entire interval, $t_2$, and stored in the memory associated with the microprocessor of the monitor/ programmer unit 42. (See blocks 78, 80 and 82.)

Next, a test is made at decision block 84 as to whether the heart was being paced or was operating in sinus rhythm during the preceding iteration. If the test shows that sinus rhythm prevailed, control follows the loop including path 86 in which the current or existing AV interval is incremented by the preprogrammed AV increment (box 88), the increment having been entered in at block 56. A test is next made at decision block 90 to determine if incrementing the AV interval causes the incremented value to exceed the preprogrammed $AV_{max}$ parameter. If not, control loops back to the input of decision block 62 and the cycle repeats with the measurement of the cardiac performance parameters being synchronized with respiratory cycles and averaged and stored in association with the AV delay value extant at the time.

When control now reaches decision block 84 on the second pass, the answer this time will be "no" since, during the cycle, the heart is being paced in one of the plural modes available and is not operating in sinus rhythm. The PR interval measured at block 54 is then examined and depending on its length, a determination is made at decision block 92 whether the patient has second or third order heart block. If not suffering from second or third degree heart block, pacing terminates and the heart is allowed to function in sinus rhythm (see block 94). If the patient had heart block, it would be programmed to operate in the VDD mode with a fixed AV interval of 100–200 ms and optimally 150 ms (block 96) and this condition would prevail thereafter since the test performed at decision block 84 would always indicate a paced mode rather than sinus rhythm.

Assuming no heart block, control will switch back and forth on successive cycles or iterations between one of the possible pacing modes and sinus rhythm. In this fashion, the system is capable of compensating for physiologic changes not attributable to the change made to the pacing parameter.

When a sufficient number of cycles have occurred such that the test at decision block 90 shows that the incremented AV interval value has exceeded the preprogrammed $AV_{max}$ parameter, the contents of the memory of the microprocessor are searched to find the maximum cardiac performance parameter, e.g., cardiac output, as well as the AV delay associated with that maximum or minimum value at the current pacing mode. See block 98. This AV delay value for the current pacing mode is then stored in the memory of the pacemaker or that of an external programmer's memory (block 100).

Next, a test is made at decision block 102 to determine if all possible modes for the pacer have been selected at block 58 and, if not, at block 104, the pacing mode is changed and control follows path 106 to the input of block 58 where the same process is carried out for determining what mode and what AV delay results in the optimum feature value. Once all modes have been exercised, the memory is again searched to find the mode and the pacing parameter yielding the optimum cardiac performance parameter (block 108) and then the pacemaker is either automatically programmed or programmed, via the monitor/ programmer module 42 and telemetry link 40, causing the implanted unit 10 to operate in the appropriate mode and with the AV interval determined to be optimum. This later operation is indicated by block 110 in the flow diagram of FIG. 2.

It can be seen, then, that following the method of the present invention, not only is the AV interval for a DDD pacemaker found which will result in optimum cardiac performance, but also the pacing mode of that pacer is likewise automatically determined. A key feature in this invention rests on the novel method of switching back to sinus rhythm between pacing periods in order to establish a baseline for comparison.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Apparatus for establishing an optimum pacing parameter value for an implantable, programmable, cardiac stimulating device, comprising:

(a) means for sensing respiratory activity of said patient;

(b) means for measuring at least one of a plurality of physiologic parameters and producing signals proportional to an average value of said at least one of said plurality of physiologic parameters over a predetermined time interval that includes an integral number of complete respiratory cycles;

(c) control means connected to said sensing means and said measuring means for incrementally changing a pacing parameter of said cardiac stimulating device by a predetermined increment value and storing said signals measured by said means for measuring associated with each incremental change of said pacing parameter until said pacing parameter reaches a predetermined limit, said control means being programmable to a plurality of pacing modes;

(d) means operatively coupled to said control means for comparing the signals stored to determine an optimum value thereof; and (e) means for sequentially selecting one of said plurality of pacing modes for said cardiac stimulating device, said measuring means, control means and comparing means being operative to determine one of a maximum and minimum value of said signals for each of said plurality of pacing modes; and (f) means for setting the pacing mode of said cardiac stimulator to the particular mode associated with said one of the maximum and minimum value of said stored signals for all of said plurality of pacing modes said pacing modes include pacing the atrium and pacing in one ventricle, pacing the atrium and pacing both ventricles, sensing the atrium and pacing one ventricle, sensing the atrium and pacing both ventricles, and pacing both atria.

2. The apparatus in claim 1 wherein said physiologic parameters include cardiac output, cardiac intervals derived from heart sounds, mean arterial pressure and pulse pressure.

3. The apparatus as in claim 1 wherein the pacing parameter being incrementally changed is selected from the group including A-V delay interval, pacing pulse width, lower rate limit of a rate adaptive cardiac stimulator, the delay between right and left atrial stimulation, and the delay between right and left ventricular stimulation.

4. The apparatus as in claim 1 wherein said measuring means periodically measures said at least one a plurality of physiologic parameters when the patient is in sinus rhythm such that said signals proportional to said average value include measurements taken when said patient is in sinus rhythm.

5. The apparatus as in claim 1 wherein said means for measuring at least one of a plurality of physiologic parameters is located external to a patient in whom said cardiac stimulating device is implanted, said apparatus further including a telemetry link operatively coupled between said means for measuring and said cardiac stimulating device.

6. A cardiac stimulating apparatus comprising:

(a) means for sensing atrial depolarization signals;

(b) means for stimulating at least one atrial chamber;

(c) means for sensing ventricular depolarization signals;

(d) means for stimulating at least one ventricular chamber;

(e) microprocessor control means coupled to said means for sensing atrial and ventricular depolarization signals, said means for stimulating at least one atrial chamber and said means for stimulating at least one ventricular chamber, said microprocessor control means including means for establishing an AV delay interval between a sensing of an atrial depolarization signal and the next subsequent stimulation of ventricular tissue;

(f) means operatively coupled to said microprocessor control means for sensing an average value of a physiologic parameter of the body during a predetermined time interval;

(g) means for periodically changing said AV delay interval and storing said average value of the physiologic parameter for each changed value of the AV delay interval by repeatedly incrementing an initial AV delay interval value until a predetermined maximum AV delay interval value is reached; and (h) means for setting the AV delay interval of the cardiac stimulating apparatus to a value producing a optimum average value of the physiologic parameter.

7. The cardiac stimulating apparatus as in claim 6 and further including said microprocessor control means programmed for providing a variety of pacing modes and means coupled to said microprocessor control means for periodically altering said pacing mode of said cardiac stimulating apparatus.

8. The cardiac stimulating apparatus as in claim 6 wherein said means for sensing an average value of the physiologic parameter include means for ensemble averaging at least one of cardiac output, heart sound determined intervals, mean atrial pressure and pulse pressure.

9. The cardiac stimulating apparatus as in claim 8 in which said predetermined time interval includes an integral number of complete respiratory cycles.

* * * * *